United States Patent
Porter, IV

(10) Patent No.: US 10,751,056 B2
(45) Date of Patent: Aug. 25, 2020

(54) METHODS AND APPARATUS FOR PERCUTANEOUS BYPASS GRAFT

(71) Applicant: High Desert Radiology, P.C., Kingman, AZ (US)

(72) Inventor: Christopher A. Porter, IV, Kingman, AZ (US)

(73) Assignee: High Desert Radiology, P.C., Kingman, AZ (US)

( * ) Notice: Subject to any disclaimer, the term of this patent is extended or adjusted under 35 U.S.C. 154(b) by 302 days.

(21) Appl. No.: 15/790,256

(22) Filed: Oct. 23, 2017

(65) Prior Publication Data

US 2019/0117226 A1 Apr. 25, 2019

(51) Int. Cl.
| | |
|---|---|
| A61B 17/11 | (2006.01) |
| A61B 1/313 | (2006.01) |
| A61F 2/848 | (2013.01) |
| A61F 2/06 | (2013.01) |
| A61F 2/08 | (2006.01) |
| A61F 2/00 | (2006.01) |

(52) U.S. Cl.
CPC .............. *A61B 17/11* (2013.01); *A61F 2/064* (2013.01); *A61F 2/848* (2013.01); *A61B 1/3137* (2013.01); *A61B 2017/1107* (2013.01); *A61B 2017/1135* (2013.01); *A61F 2/0027* (2013.01); *A61F 2002/061* (2013.01); *A61F 2002/0829* (2013.01); *A61F 2220/0025* (2013.01)

(58) Field of Classification Search
CPC ............ A61B 17/11; A61B 2017/1107; A61B 2017/1135; A61B 2017/1132; A61B 2017/1139; A61F 2/064; A61F 2/848; A61F 2002/8483; A61F 2002/8486; A61F 2002/0025; A61F 2002/0033
See application file for complete search history.

(56) References Cited

U.S. PATENT DOCUMENTS

| | | |
|---|---|---|
| 5,250,033 A | 10/1993 | Evans et al. |
| 5,443,497 A | 8/1995 | Venbrux |
| 5,695,504 A | 12/1997 | Gifford, III et al. |
| 5,755,775 A | 5/1998 | Trerotola et al. |
| 5,799,661 A | 9/1998 | Boyd et al. |
| 5,989,276 A | 11/1999 | Houser et al. |
| 6,035,856 A | 3/2000 | LaFontaine et al. |
| 6,113,612 A | 9/2000 | Swanson et al. |

(Continued)

OTHER PUBLICATIONS

John R. Ross, MD, "Percutaneous Venous Anastomosis with a Hybrid Vascular Graft," Endovascular Today, Jun. 2012, pp. 44-48.

(Continued)

*Primary Examiner* — Diane D Yabut
*Assistant Examiner* — Majid Jamialahmadi
(74) *Attorney, Agent, or Firm* — The Noblitt Group, PLLC

(57) ABSTRACT

Methods and apparatus for a percutaneous bypass graft system according to various aspects of the present technology include a graft section comprising a dual-sided fixation system at the anastomosis site and a tamper sheath configured to provide enhanced control during installation. The dual-sided fixation system may comprise a plurality of barbs configured to secure the graft section to an internal and external portion of a target vessel. The tamper sheath comprises a cuff at a distal end that is configured to be positioned against an outer surface of the target vessel during the percutaneous procedure.

13 Claims, 11 Drawing Sheets

(56) References Cited

U.S. PATENT DOCUMENTS

| | | |
|---|---|---|
| 6,293,955 B1 | 9/2001 | Houser et al. |
| 6,451,048 B1* | 9/2002 | Berg ................. A61F 2/064 |
| | | 606/153 |
| 6,485,513 B1 | 11/2002 | Fan |
| 6,524,322 B1 | 2/2003 | Berreklouw |
| 7,351,247 B2 | 4/2008 | Kupiecki et al. |
| 8,282,664 B2 | 10/2012 | Nance et al. |
| 8,579,932 B2 | 11/2013 | Pantages et al. |
| 9,649,112 B2 | 5/2017 | Asfora et al. |
| 2001/0004699 A1 | 6/2001 | Gittings et al. |
| 2002/0032462 A1 | 3/2002 | Houser et al. |
| 2002/0099393 A1 | 7/2002 | Fleischman et al. |
| 2005/0216043 A1 | 9/2005 | Blatter et al. |
| 2010/0204776 A1 | 8/2010 | Anwar et al. |
| 2012/0150274 A1* | 6/2012 | Shalev ................ A61F 2/856 |
| | | 623/1.12 |
| 2014/0046429 A1 | 2/2014 | Cragg et al. |
| 2014/0088623 A1 | 3/2014 | Yevzlin et al. |
| 2015/0134051 A1 | 5/2015 | Donadio et al. |
| 2017/0128072 A1 | 5/2017 | Wang et al. |

OTHER PUBLICATIONS

Pressure Products, "SafeSheath® Ultra Hemostatic Peel-away Introducer System for Vascular Access," www.pressure-products, com, accessed Oct. 16, 2017.

Pressure Products, "Hemostatic Peel-Away Introducer System for Vascular Access," www.pressure-products,com, accessed Oct. 16, 2017.

\* cited by examiner

METHODS AND APPARATUS FOR PERCUTANEOUS BYPASS GRAFT

BACKGROUND OF THE TECHNOLOGY

Various methods of creating arterial/venous bypasses exist and may include surgical intervention. Surgical options often require cutting-down onto the target vessel. Surgical options are more invasive and time consuming, often causing more trauma to the target vessel, increasing both procedure and recovery times. Efforts to create a less invasive method of bypassing occlusions, reducing recovery and procedure times has resulted in percutaneous procedures that allow a graft to be created without open surgery by accessing a vessel percutaneously (through the skin).

Though rudimentary percutaneous methods have been developed, there remain issues with obtaining a proper seal at the anastomosis site to prevent leakage. Without a proper seal on the target vessel, the graft may not function properly and result in high risks of morbidity and additional invasive procedures.

SUMMARY OF THE TECHNOLOGY

Methods and apparatus for a percutaneous bypass graft system according to various aspects of the present technology include a graft section comprising a dual-sided fixation system at the anastomosis site and a tamper sheath configured to provide enhanced control during installation. The dual-sided fixation system may comprise a plurality of fixation barbs and cuffs configured to secure the graft section to the internal and external portion of the target vessel. The tamper sheath comprises a cuff at a distal end that is configured to be positioned against an outer surface of the target vessel during the percutaneous procedure to ensure proper sealing.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Figure 1A:
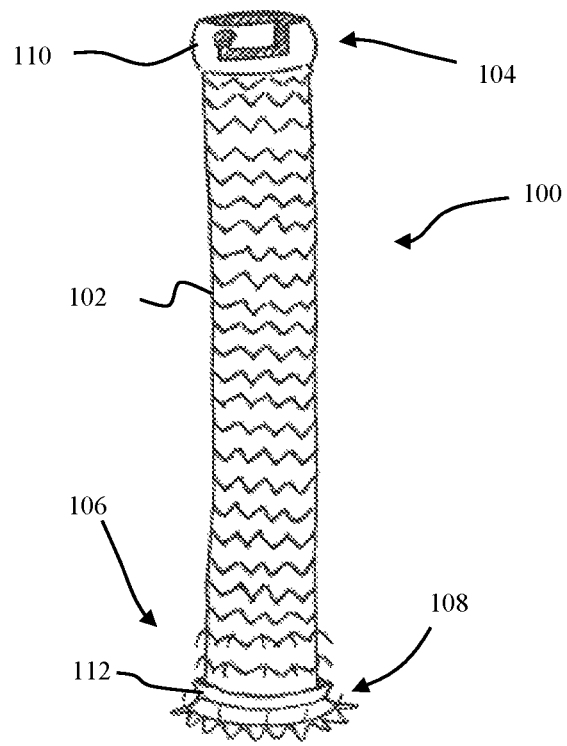
FIG. 1A representatively illustrates an unconstrained graft device in accordance with an exemplary embodiment of the present technology.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of hardware components configured to perform the specified functions and achieve the various results. For example, the present technology may employ various materials, needles, injectable devices, dilators, grafts, and the like, which may carry out a variety functions. In addition, the present technology may be practiced in conjunction with any number of applications, and the system described is merely one exemplary application for the technology.

Referring now to FIGS. 1A, 1B, 16, and 17, a graft device 100 according to various aspects of the present technology may comprise a substantially tubular body 102 having a first end 104 and a second end 106. The graft device 100 may comprise any suitable system or apparatus for forming a bypass anastomosis for a vessel such as an artery or vein. For example, the first end 104 of the graft device 100 may comprise a coupler 110 configured to attach or otherwise selectively connect the graft device 100 to a secondary device such as a second graft device 100B or a bypass graft section 1600. The second end 106 of the graft device 100 may comprise a fixation system 108 configured to secure the second end 106 to a wall of the vessel and a sealing cuff 118.

The coupler 110 allows the graft device 100 to be selectively connected to the bypass graft section 1600. The coupler 110 may comprise any suitable system or method for connecting the graft device 100 to the bypass graft section 1600. For example, in one embodiment, the coupler 110 may comprise a housing having a channel 112 suitably configured to receive and secure a mating protrusion from the separate section of the graft system. In an alternative embodiment, the coupler 110 may be suitably configured to receive a conduit portion of the separate section within an interior section. The coupler 110 and the separate section may then be coupled together by a mechanical fastener or fused together through an adhesive or bonding process.

The fixation system 108 secures the graft device 100 to the vessel to prevent separation and reduce or eliminate leakage at the anastomosis site. The fixation system 108 may comprise any suitable device to connect the second end 106 of the graft device 100 to the wall of the vessel. The fixation system 108 may also be suitably configured to create an anastomotic seal to create a more leak resistant seal. Referring now to FIGS. 1B and 2-4, in one embodiment, the fixation system may comprise a first fixation device 114 configured to engage an interior surface 404 of the vessel wall 402 and a second fixation device 116 configured to engaged an exterior surface 406 of the vessel wall 402.

The first fixation device 114 engages and secures the second end 106 of the graft device 100 to the interior surface 404 of a target vessel 400 at the anastomosis site. The first fixation device 114 may comprise any suitable system or device for fixedly positioning the graft device 100 to the target vessel 400. In one embodiment, the first fixation device 114 may comprise a plurality of barbs 202 extending outwardly from a perimeter of a flange 204 extending outwardly from the sealing cuff 118 at the second end 106. The barbs 202 may extend away from the flange 204 in a manner to come into contact with and extend at least partially into the interior surface 404 of the vessel wall 402. For example, the flange 204 may be suitably configured to form a diameter $D_3$ that is larger than a diameter $D_1$ of an opening created in the target vessel 400 and the barbs 202 may be positioned on the flange 202 such that when the flange 204 is brought into contact with the interior surface 404 of the vessel wall 402, the barbs 202 extend into the vessel wall 402. The barbs 202 may help permanently affix the flange 204 to the interior surface 404 of the vessel wall 402 or the barbs 202 may help keep the flange 204 in place until the flange 204 is adhered to the interior surface 404 of the vessel wall 402 through any suitable mechanism.

The barbs 202 may be straight or they may comprise a slight arc shape. For example, the barbs 202 may be slightly bent to create an arc shape that is generally pointed back towards the first end 104 of the graft device 100. The bend in the barbs 202 may help create a stronger bond between the barbs 202 and the vessel wall 402.

The barbs 202 may comprise any suitable medical grade material for use with a desired type of vessel. The barbs 202 may also comprise any suitable length and may be configured to extend only part way into the vessel wall 402. Alternatively, the barbs 202 may comprise a length capable of extending completely through the vessel wall 402 so that at least a portion of each barb 202 extends outward from the exterior surface 406 of the vessel wall 402.

The second fixation device 116 engages and secures the second end 106 of the graft device 100 to the exterior surface 406 of the vessel wall 402 at the anastomosis site. The second fixation device 116 may comprise any suitable system or device for fixedly positioning the graft device 100 to the target vessel 400. In one embodiment, the second fixation device 116 may comprise a second plurality of barbs 302 extending outwardly from an outer perimeter of the second end 106 proximate the first plurality of barbs 202. The second plurality of barbs 302 may be separated from the first plurality of barbs 202 by a distance sufficient to allow the vessel wall 402 to be positioned therebetween.

The second plurality of barbs 302 may extend away from the body 102 in a manner to come into contact with and extend at least partially into the exterior surface 406 of the vessel wall 402. For example, the second plurality of barbs 302 may be slightly bent to create an arc shape that is generally pointed towards the second end 106 of the graft device 100. The second plurality of barbs 302 may further be arranged to create a more secure connection than the first plurality of barbs 202. For example, the second plurality of barbs 302 may comprise two adjacent rows of barbs 302 with each row having a slightly different distance from the first plurality of barbs 202.

The sealing cuff 118 encourages hemostasis/sealing at the anastomosis. The sealing cuff 118 may comprise any suitable device or system for helping reduce potential for leakage. Referring again to FIGS. 2, 3, and 4, in one embodiment, the sealing cuff 118 may comprise a lipped edge portion 206 having a diameter $D_2$ that is larger than the diameter $D_1$ of the opening in the target vessel 400 but smaller than $D_3$. The lipped edge portion 206 is configured to sit against, or otherwise engage the interior surface 404 of the vessel wall 402 at a location between the flange 204 and the opening in the target vessel 400. The lipped edge portion 206 may seal the opening and prevent leakage.

The graft device 100 may comprise any suitable dimensions according to a desired application such as the type of artery/vein requiring the anastomosis and the location within the body. For example, the body 102 of the graft device 100 may comprise any suitable diameter between about 0.2 millimeters and about 15.0 millimeters to allow as similar a flow rate as possible to that of the target vessel 400.

The graft device 100 may comprise any suitable material or combinations of materials suitable for use inside the human body such as natural or synthetic polymers or metal alloys. For example, in one embodiment, the body 102 may comprise a material such as nitinol and the coupler 110 may comprise a plastic such as polytetrafluoroethylene (PTFE).

Figure 1B:
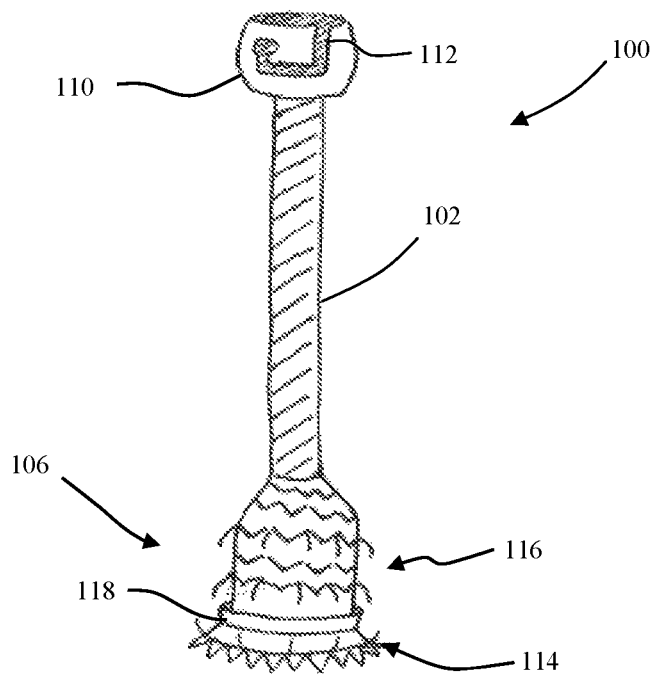
FIG. 1B representatively illustrates a partially constrained graft device in accordance with an exemplary embodiment of the present technology.
Figure 2:
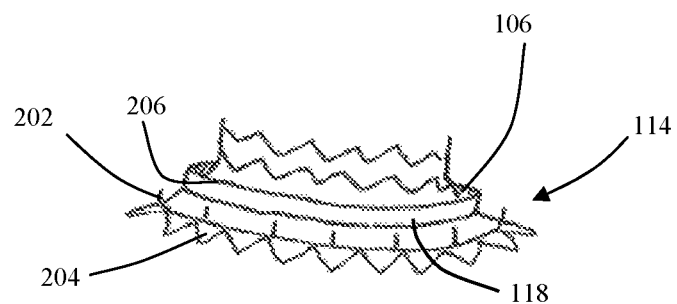
FIG. 2 representatively illustrates a detailed view of a set of internal fixation barbs and a cuff in accordance with an exemplary embodiment of the present technology.
Figure 3:
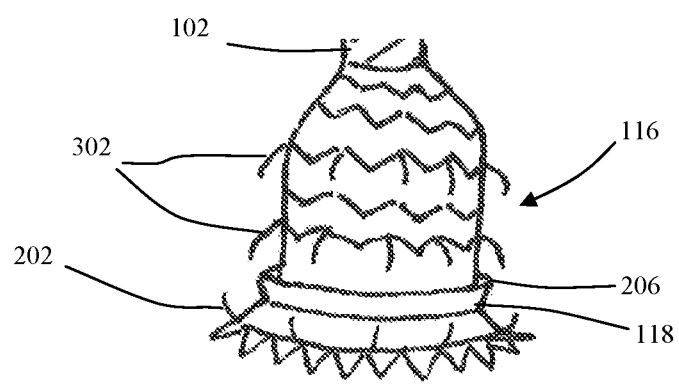
FIG. 3 representatively illustrates a detailed view of a set of external fixation barbs positioned proximal to the internal fixation barbs in accordance with an exemplary embodiment of the present technology.
Figure 4:
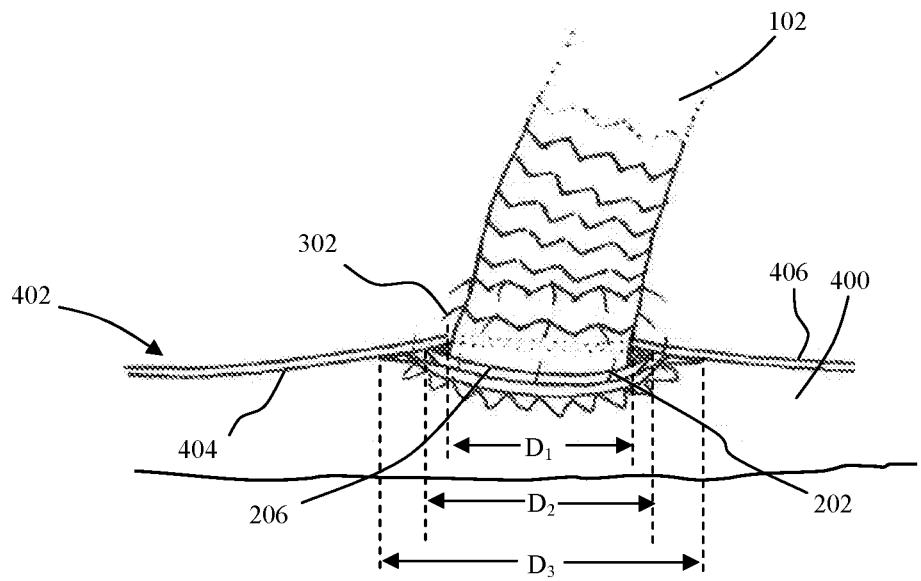
FIG. 4 representatively illustrates a detailed view of the internal and external fixation barbs interfacing with the vessel wall in accordance with an exemplary embodiment of the present technology.

Referring again to FIGS. 1A and 1B, the graft device 100 may comprise different interior dimensions before and after installation. For example, prior to installation, the body 102 of the graft device 100 may be constrained to a first interior diameter (FIG. 1B). This first interior diameter may ease installation by allowing the graft device to fit easier into an introducer sheath and/or by allowing the graft device 100 to be more rigid. Once positioned, the body 102 may be unconstrained and expanded to a second operational diameter (FIG. 1A).

The graft device 100 may be deployed into the target vessel 400 by any suitable method or process. A series of tear away sheaths and commonly known percutaneous access devices such as needles, vascular dilators, and guide wires may be utilized to position and install the graft device 100.

Figure 5:
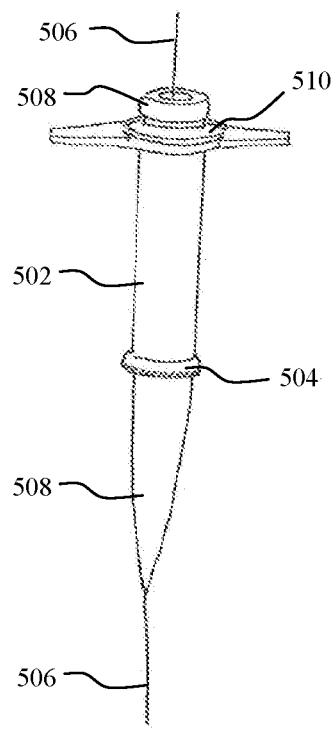
FIG. 5 representatively illustrates a tamper sheath and a transitional dilator in accordance with an exemplary embodiment of the present technology.

Referring now to FIG. 5, a tamper sheath 502 is used to position the graft device 100 in place and aid in seating of the internal fixation device 114 to create a leak resistant anastomotic seal. The tamper sheath 502 is similar in function to common introducer sheaths and is configured to work with standard percutaneous devices such as a guide wire 506 that is positioned in the target vessel 400 by an access needle (not shown) and a vascular dilator 508. The tamper sheath 502 may also be configured to function as a tear-away sheath to facilitate removal. The tamper sheath 502 may comprise an insertion end 510 that is configured to receive the vascular dilator 508, a distal end having a cuff 504 that is configured to be positioned against the exterior surface 406 of the vessel wall 402, and a lumen extending between the insertion end 510 and the distal end.

The cuff 504 helps seal the opening after the vascular dilator 508 is removed. The cuff 504 may comprise any suitable system or device for helping provide a seal at the anastomosis site. For example, in one embodiment, the cuff 504 may comprise a thicker wall section at the end of the tamper sheath 502. Alternatively, the cuff 504 may comprise an inflatable end portion (not shown) that is configured to be inflated to create a seal at the anastomosis site during the procedure. In a third embodiment, the cuff 504 may comprise a detachable sealing ring (not shown) that is configured to be left behind and against the exterior surface of the vessel wall 402 when the tamper sheath 502 is removed.

Figure 6:
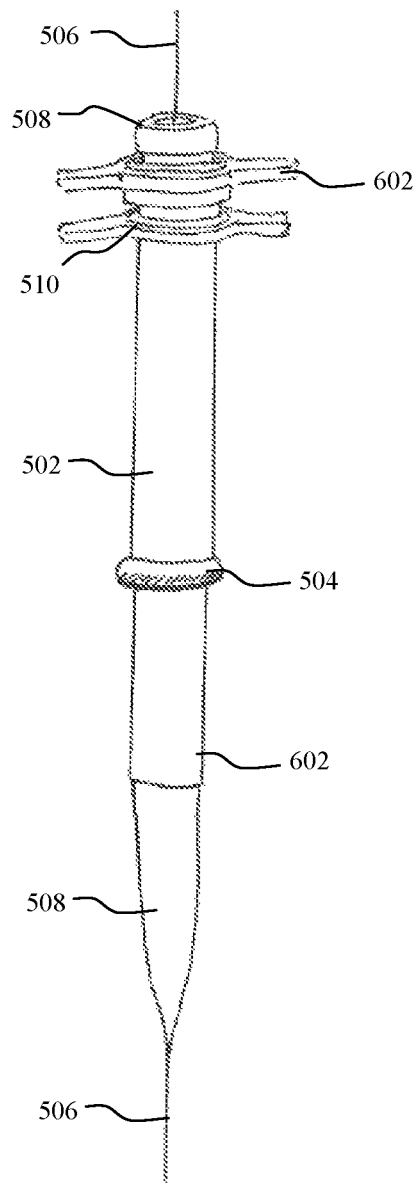
FIG. 6 representatively illustrates a deployment sheath positioned between the tamper sheath and the transitional dilator in accordance with an exemplary embodiment of the present technology.
Figure 7:
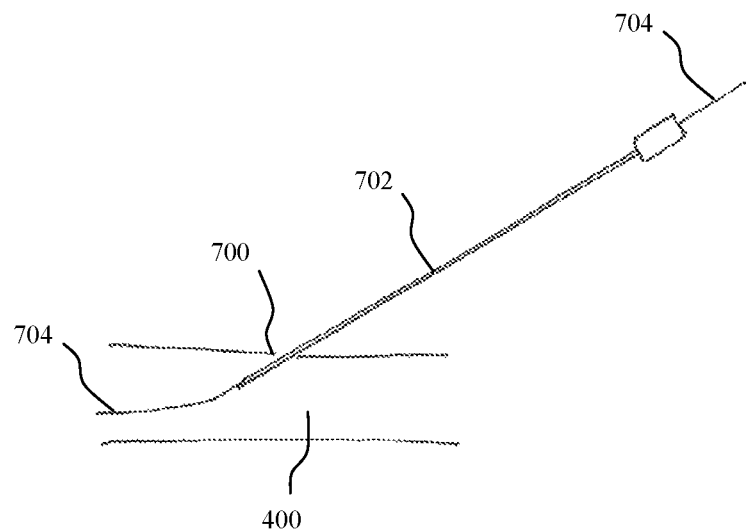
FIG. 7 representatively illustrates percutaneous access of a target vessel in accordance with an exemplary embodiment of the present technology.

Referring now to FIG. 6, a deployment sheath 602 may be used to form an access lumen into the target vessel 400. The deployment sheath 602 may be suitably configured to be inserted into the insertion end 510 of the tamper sheath 502 and fit over the dilator 508. Similar to the tamper sheath 502, the deployment sheath 602 may be configured to function as a tear-away sheath to facilitate removal after the graft device 100 is installed.

Figure 16:
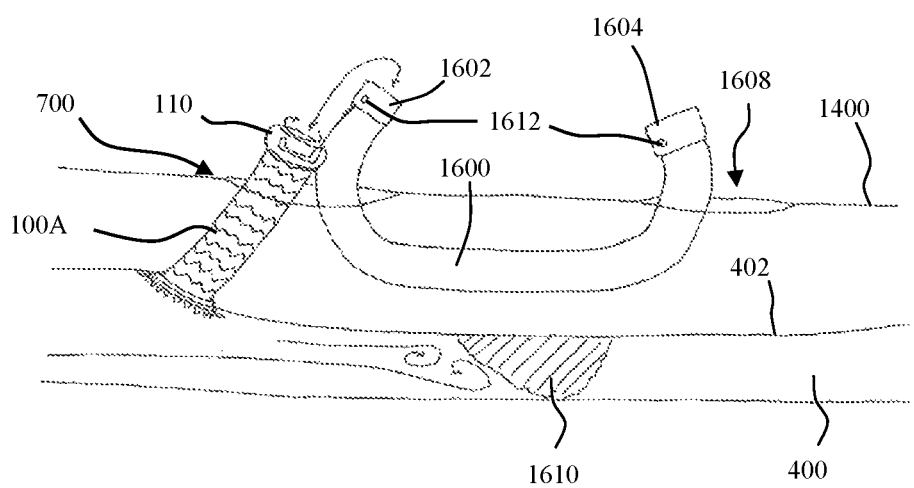
FIG. 16 representatively illustrates a bypass graft section in accordance with an exemplary embodiment of the present technology.
Figure 17:
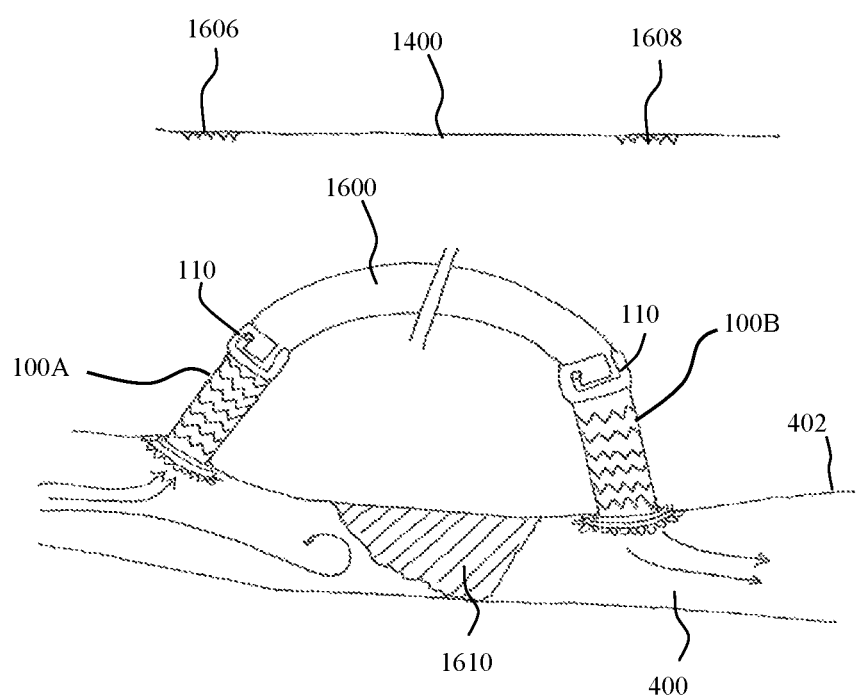
FIG. 17 representatively illustrates installed proximal and distal graft devices attached via subcutaneous graft coupler to the target vessel in accordance with an exemplary embodiment of the present technology.
Figure 18:
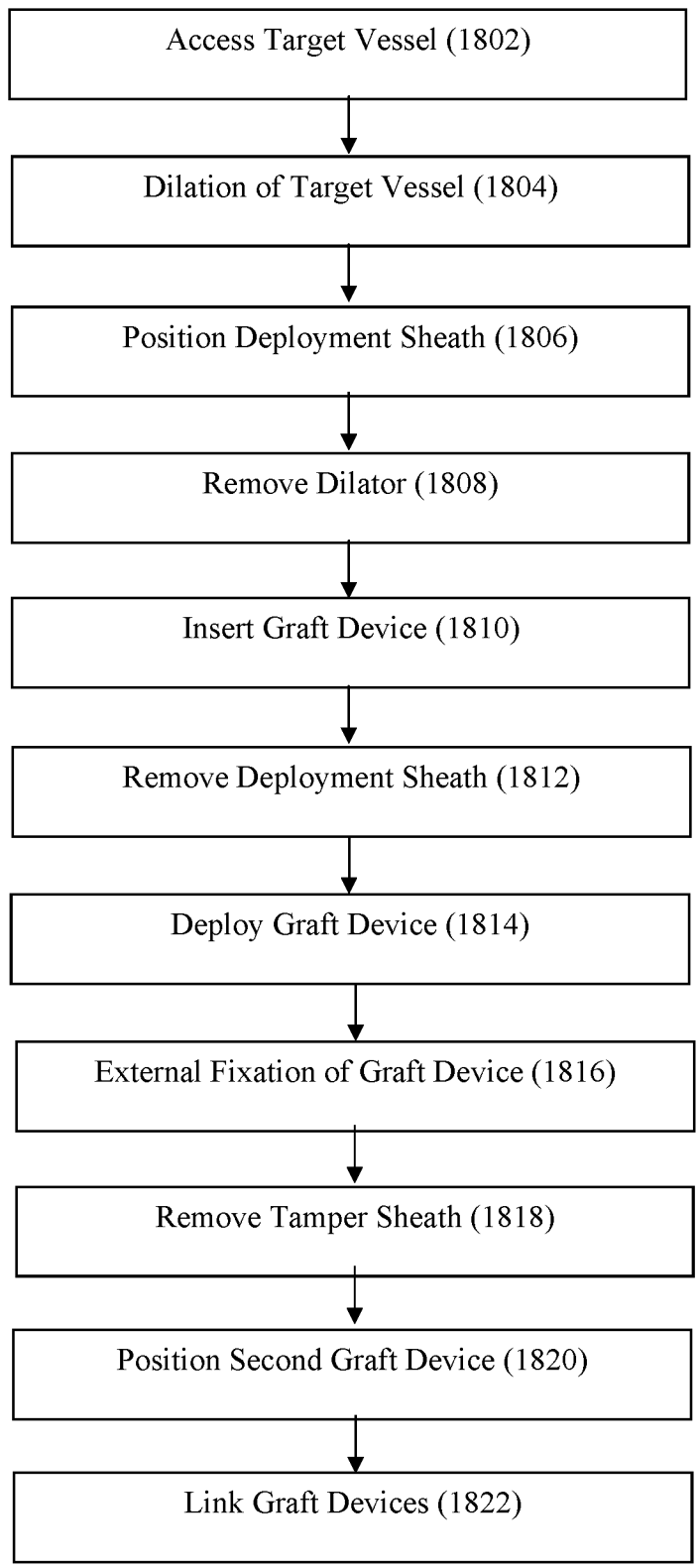
FIG. 18 is a flowchart of the installation process in accordance with an exemplary embodiment of the present technology.

Referring now to FIGS. 16 and 17, the coupler 110 of the graft device 100 is configured to connect the graft device 100 to the bypass graft section 1600. The bypass graft section 1600 may comprise any suitable device for providing a lumen or conduit for fluid flow around a blockage 1610 or hemodynamically significant stenosis within the target vessel 400. Alternatively, the bypass graft section 1600 may compromise any suitable device for providing a lumen or conduit to create a vascular fistula. The bypass graft section 1600 may comprise similar materials to those of the graft device 100 since it is intended for use under the skin 1400. The bypass graft section 1600 may also comprise any suitable length to accommodate a desired bypass path around the blockage 1610 or hemodynamically significant stenosis.

Each end of the bypass graft section 1600 may comprise a coupling element 1602, 1604 suitably configured to be selectively connected to the coupler 110 of first and second graft sections 100A, 100B. The coupling elements 1602, 1604 may be configured to universally mate with the coupler 110 of the graft device 100. For example, the coupling elements 1602, 1604 may comprise an end section configured to fit within the coupler 110. A protrusion 1612 may extend outwardly from an exterior surface of the coupling elements 1602, 1604 that is sized to fit within the channel 112 of the coupler 110 and lock the bypass graft section 1600 to the graft device 100. In an alternative embodiment, the coupling elements 1602, 1604 may be configured slightly differently from each other so that a first coupling element 1602 only mates to the first graft device 100A and a second coupling element 1604 only mates to the second graft device 100B. For example, the bypass graft section 1600 maybe suitably configured to provide proper flow in a single direction. Therefore, by creating individualized coupling elements 1602, 1604 proper orientation of the bypass graft section may be achieved.

Figure 8:
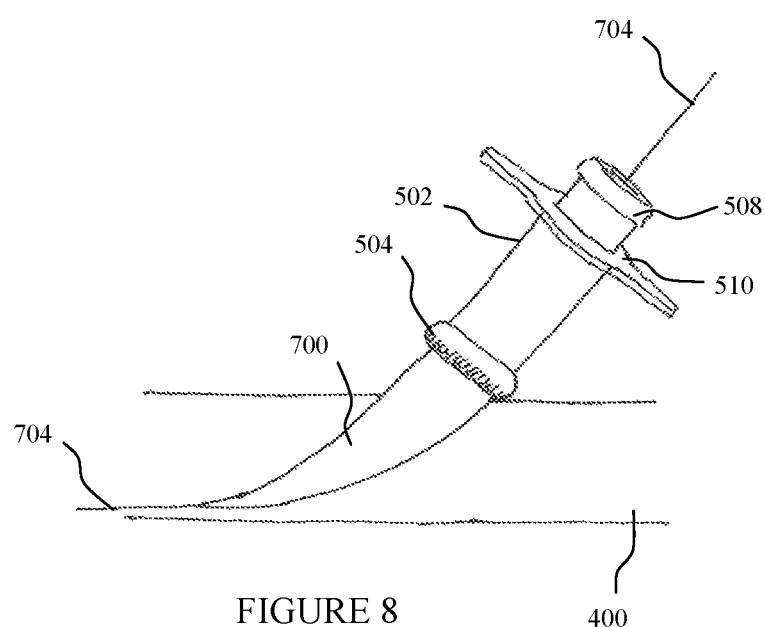
FIG. 8 representatively illustrates dilation of the target vessel in accordance with an exemplary embodiment of the present technology.

In operation and referring now to FIGS. 7-18, a percutaneous bypass graft is created by securing a first graft device 100 at a first location of a target vessel 400, securing a second graft device 100 at a second location of a target vessel 400, and linking the two graft devices 100 with a bypass graft section 1600. This may be achieved through a combined use of known methods of percutaneous access to a vessel and use of the disclosed graft device 100 and improved sheaths. For example, a first anastomosis site 700 may be identified on a target vessel 400 and an access needle 702 may be inserted into an interior of the target vessel. A guide wire 704 may be inserted through the access needle 702 and into the target vessel 400 (FIG. 7) (1802). The access needle 702 may then be removed and dilation of the target vessel 400 may be performed by sliding a tamper sheath 502 over the guide wire 704 and positioning the tamper sheath 502 adjacent to the target vessel 400 (FIG. 8). A dilator 508 may slid over the guide wire 704 and then insert into the lumen of the tamper sheath 502 through the insertion end 510 and allowed to follow the guide wire 704 into the target vessel 400 (1804).

Figure 9:
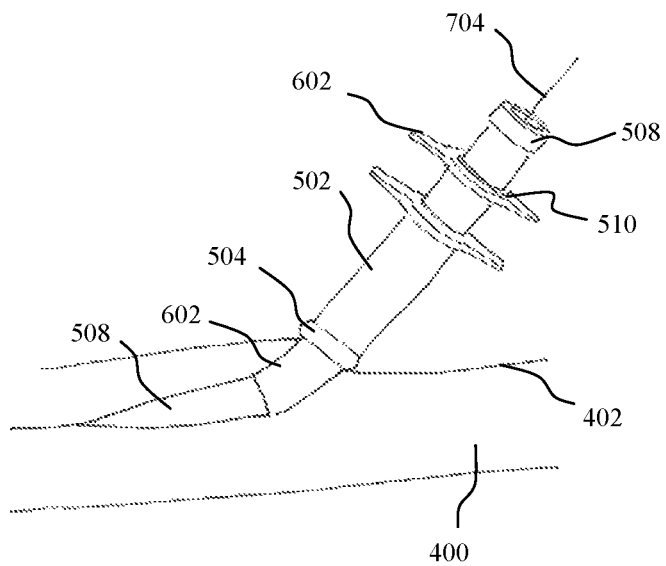
FIG. 9 representatively illustrates a deployment sheath extending into the target vessel in accordance with an exemplary embodiment of the present technology.
Figure 10:
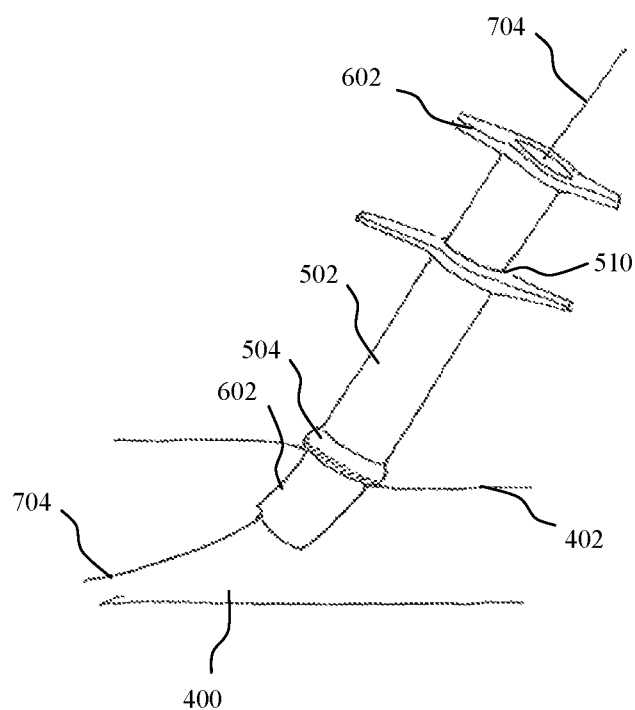
FIG. 10 representatively illustrates the deployment sheath within the target vessel and tamper sheath outside the target vessel status post removal of the transitional dilator in accordance with an exemplary embodiment of the present technology.

A cuff 504 of the tamper sheath 502 is positioned against an exterior surface 406 of the vessel wall 402 and a deployment sheath 602, positioned between the dilator 508 and tamper sheath 502, is slid into the lumen of the target vessel (FIG. 9). The dilator 508 may then be removed from the target vessel 400 by sliding it outwardly away from the insertion end 510 of the tamper sheath 502 (FIG. 10) leaving the guide wire 704, deployment sheath 602, and tamper sheath 502 behind (1808).

Figure 11:
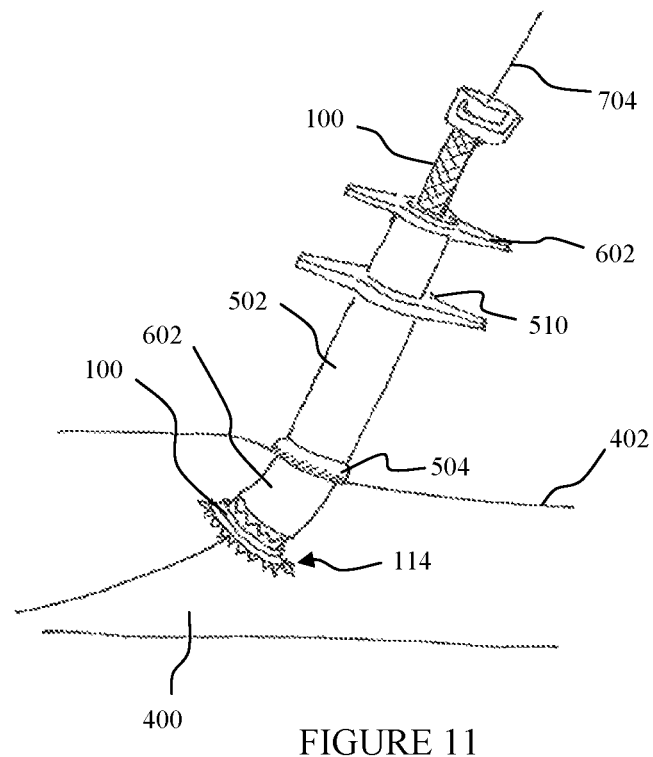
FIG. 11 representatively illustrates a partially constrained graft device inserted through the deployment sheath in accordance with an exemplary embodiment of the present technology.
Figure 12:
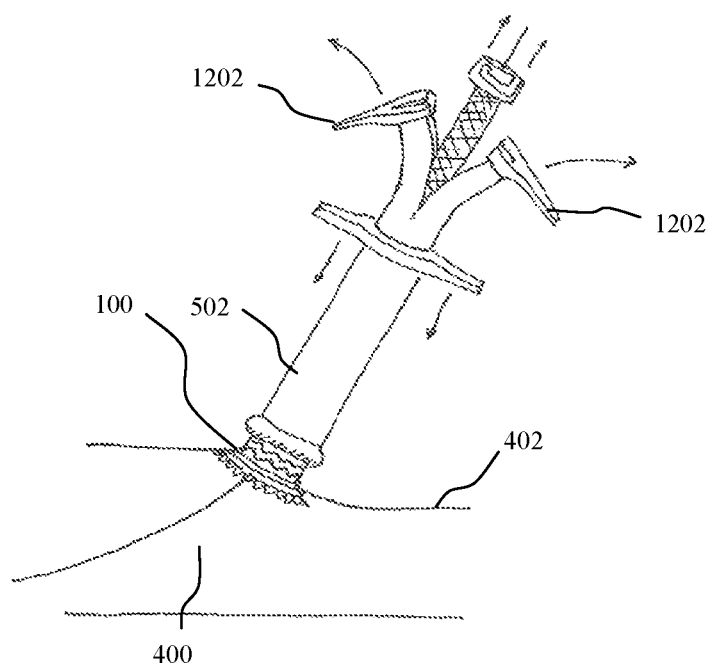
FIG. 12 representatively illustrates removal of a tear-away deployment sheath in accordance with an exemplary embodiment of the present technology.
Figure 13:
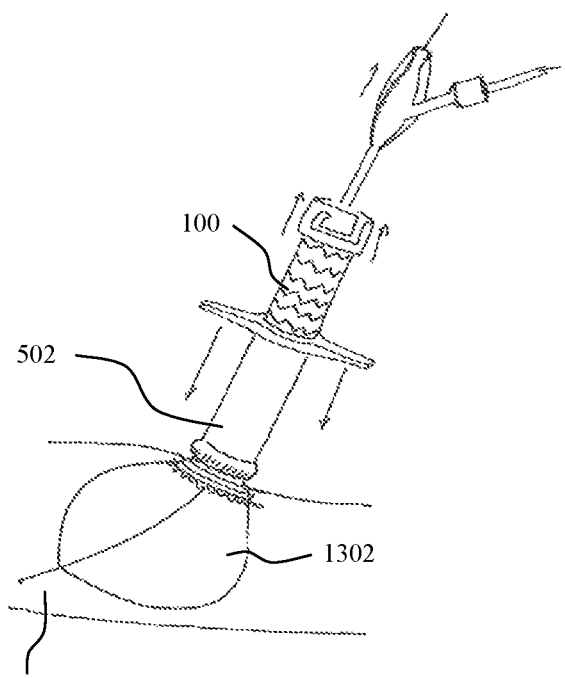
FIG. 13 representatively illustrates a compliant balloon dilitation of the arterial anastomosis with simultaneous forward tamper sheath pressure to seat the internal fixation barbs/cuff to the target vessel in accordance with an exemplary embodiment of the present technology.

The graft device 100 is then positioned over the guide wire 704 and slid into the deployment sheath 602 (FIG. 11). The graft device 100 extends completely through the deployment sheath 602 and into the target vessel 400 (1810) until the internal fixation device 114 is exposed. After the graft device 100 is positioned, the deployment sheath 602 may be removed (FIG. 12). Removal may be accomplished by tearing apart two end pieces 1202 of the deployment sheath 602. The deployment sheath 602 may then be slid out of the tamper sheath 502 while applying slight forward pressure on the tamper sheath 502 to maintain its position (1812) and appose the internal fixation device 114 to the internal surface of a target vessel 404. A compliant balloon 1302 can also be placed within the graft 100, over the guidewire 704, and insufflated within the vessel to further appose the internal fixation device 114 against the internal surface of the target vessel 404.

Figure 14:
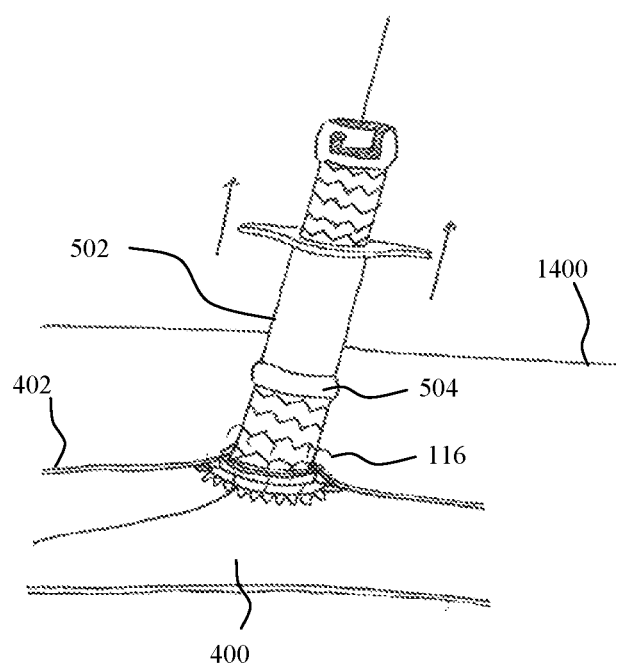
FIG. 14 representatively illustrates posterior traction of the device with simultaneous removal of tamper sheath to deploy external fixation barbs into the perivascular soft tissues in accordance with an exemplary embodiment of the present technology.

The graft device 100 may then be converted from a partially constrained state of a reduced interior diameter to its full operational diameter by releasing a constraining tether (FIG. 13) (1814). Once the graft device 100 has achieved its full working diameter, the balloon 1302 may be removed and the second fixation device 116 exposed (FIG. 14). This may be accomplished by moving the cuff 504 of the tamper sheath 502 away from the vessel wall 402 and towards the skin 1400, while maintaining gentle traction on the unconstrained graft, so that the second fixation device 116 is exposed and allowed to engage or otherwise come into contact with the external surface 406 of the vessel wall 402 (1816).

Figure 15:
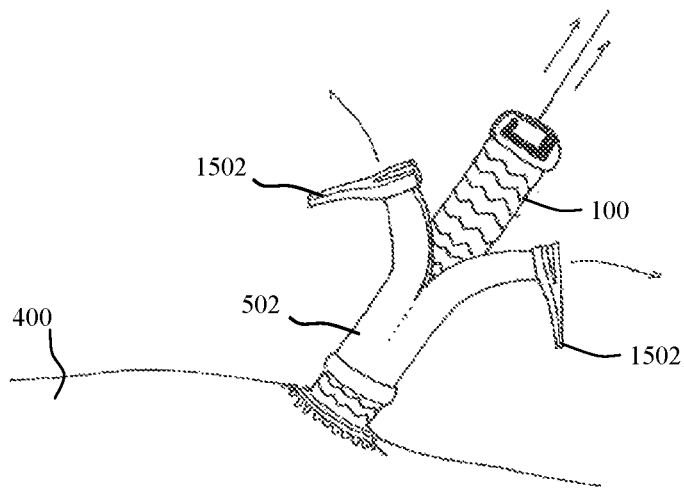
FIG. 15 representatively illustrates removal of tear-away tamper sheath in accordance with an exemplary embodiment of the present technology.

After the second fixation device 116 is positioned against the external surface 406 of the vessel wall 402, the tamper sheath 502 and the guide wire 704 may be removed (FIG. 15). Removal may be accomplished by tearing apart two end pieces 1502 of the tamper sheath 502 (1818). The graft device 100 is the only portion of the installation system left in place and secured to the target vessel.

Referring now to FIGS. 16 and 17, the graft device 100 is commonly positioned on a first side of a blockage 1610 at the first anastomosis site 700. A second anastomosis site 1608 is identified at a location near the target vessel 400 on the other side of the blockage 1610. Alternatively, the graft device 100 can also be positioned to create a fistulous connection between two vessels. A bypass graft section 1600 is tunneled under the skin 1400 from the first anastomosis site 700 to the second anastomosis site 1608. A second graft device 100B may then be attached to the target vessel 400 according to the preceding steps for the first graft device 100A (1820).

After the first and second graft devices 100A, 100B are connected to the target vessel 400, they may be linked together by the bypass graft section 1600 (1822). A first coupling element 1602 on the bypass graft section 1600 may be connected to the coupler 110 of the first graft device 100A. A second coupling element 1604 of the bypass graft section 1600 may then be connected in a similar manner to the second graft device 100B completing the bypass. Sutures 1606, 1608 may be used to close dermatotomies created for placing the first and second anastomoses 700, 1608 thereby positioning the graft devices 100A, 100B and the bypass graft section 1600 completely under the skin 1400.

These and other embodiments for methods of forming an attachment system for a syringe may incorporate concepts, embodiments, and configurations as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology, as expressed in the following claims.

The invention claimed is:

1. A system for percutaneous vessel anastomosis, comprising:
    a tamper sheath comprising:
        an insertion end;
        a distal end having a cuff; and
        a lumen extending between the insertion end and the distal end;
    a deployment sheath configured to be selectively inserted into the insertion end and extend into a vessel through the distal end, wherein the deployment sheath comprises a second lumen extending between opposing ends of the deployment sheath; and
    a graft device having a generally tubular body section configured to be selectively inserted into the second lumen and extend into the vessel, wherein the graft device comprises:
        a coupler disposed at a first end of the graft device; and
        a fixation system disposed at a second end of the graft device, wherein the fixation system comprises:
            a first fixation device configured to secure the graft device to an internal surface of the vessel; and
            a second fixation device configured to secure the graft device to an external surface of the vessel.

2. A system for percutaneous vessel anastomosis according to claim 1, wherein:
    the first fixation device comprises a first plurality of barbs extending outwardly from an outer perimeter of the graft device at the second end; and
    the second fixation device comprises a second plurality of barbs extending outwardly from the outer perimeter of the graft device proximate the first plurality of barbs, wherein the first and second plurality of barbs are separated by a distance sufficient to allow a wall of the vessel to be positioned therebetween.

3. A system for percutaneous vessel anastomosis according to claim 2, wherein the first plurality of barbs are bent towards the first end of the graft device to engage the internal surface of the vessel.

4. A system for percutaneous vessel anastomosis according to claim 2, wherein the second plurality of barbs are bent towards the second end of the graft device to engage the external surface of the vessel.

5. A system for percutaneous vessel anastomosis according to claim 2, wherein the second plurality of barbs comprise at least two adjacent rows of barbs.

6. A system for percutaneous vessel anastomosis according to claim 2, wherein the graft device further comprises a lipped edge portion positioned between the first plurality of barbs and the outer perimeter of the graft device at the second end.

7. A system for percutaneous vessel anastomosis according to claim 1, further comprising a bypass graft section configured to link the graft device to a second graft device.

8. A system for percutaneous vessel anastomosis according to claim 7, wherein the coupler comprises a connector configured to mate to a mating connector from the bypass graft section.

9. A system for percutaneous vessel anastomosis according to claim 1, wherein the cuff is inflatable.

10. A graft device for a blood vessel, comprising:
a generally tubular body section having first and second ends, wherein:
a coupler is disposed at the first end and is configured to connect the first end of the generally tubular body section to a mating coupler of a secondary graft device; and
a fixation system is disposed at the second end, wherein the fixation system comprises:
a first fixation device comprising a first plurality of barbs extending outwardly from an outer perimeter of the graft device at the second end to secure the graft device to an internal surface of the vessel; and
a second fixation device comprising a second plurality of barbs arranged in at least two adjacent rows and extending outwardly from the outer perimeter of the graft device proximate the first plurality of barbs to secure the graft device to an external surface of the vessel, wherein the first and second plurality of barbs are separated by a distance sufficient to allow a wall of the vessel to be positioned therebetween.

11. A graft device according to claim 10, wherein the first plurality of barbs are bent towards the first end of the graft device to engage the internal surface of the vessel.

12. A graft device according to claim 10, wherein the second plurality of barbs are bent towards the second end of the graft device to engage the external surface of the vessel.

13. A graft device according to claim 10, wherein the graft device further comprises a lipped edge portion positioned between the first plurality of barbs and the outer perimeter of the graft device at the second end.

* * * * *